(12) United States Patent
Wu et al.

(10) Patent No.: US 11,273,205 B2
(45) Date of Patent: Mar. 15, 2022

(54) IL-15 PROTEIN COMPLEX PHARMACEUTICAL COMPOSITION

(71) Applicants: JIANGSU HENGRUI MEDICINE CO., LTD., Jiangsu (CN); SHANGHAI HENGRUI PHARMACEUTICAL CO., LTD., Shanghai (CN)

(72) Inventors: Tingting Wu, Shanghai (CN); Hao Li, Shanghai (CN); Xun Liu, Shanghai (CN)

(73) Assignees: JIANGSU HENGRUI MEDICINE CO., LTD., Jiangsu (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 16/632,411

(22) PCT Filed: Jul. 24, 2018

(86) PCT No.: PCT/CN2018/096775
§ 371 (c)(1),
(2) Date: Jan. 20, 2020

(87) PCT Pub. No.: WO2019/019998
PCT Pub. Date: Jan. 31, 2019

(65) Prior Publication Data
US 2020/0230210 A1 Jul. 23, 2020

(30) Foreign Application Priority Data

Jul. 25, 2017 (CN) .......................... 201710611317.2

(51) Int. Cl.
*A61K 38/20* (2006.01)
*A61K 9/19* (2006.01)
*A61K 38/17* (2006.01)

(52) U.S. Cl.
CPC ............ *A61K 38/2086* (2013.01); *A61K 9/19* (2013.01); *A61K 38/1793* (2013.01)

(58) Field of Classification Search
CPC ..................................................... A61K 9/19
See application file for complete search history.

(56) References Cited

U.S. PATENT DOCUMENTS

| 10,206,980 B2 * | 2/2019 | Qu ........................ A61P 35/00 |
| 10,905,743 B2 * | 2/2021 | Qu ........................ A61P 17/00 |
| 2007/0160578 A1 | 7/2007 | Waldmann et al. |
| 2009/0060906 A1 * | 3/2009 | Barry ..................... A61K 47/20 |
| | | 424/131.1 |
| 2015/0359853 A1 * | 12/2015 | Felber ..................... A61P 31/18 |
| | | 424/85.2 |

FOREIGN PATENT DOCUMENTS

| CN | 1760209 A | 4/2006 |
| CN | 101172100 A | 5/2008 |
| CN | 101600457 A | 12/2009 |
| CN | 103370339 A | 10/2013 |
| CN | 105708811 A | 6/2016 |
| WO | 2016095642 A1 | 6/2016 |
| WO | WO-2016095642 A1 * | 6/2016 ............. A61P 37/02 |

OTHER PUBLICATIONS

"Best Practices in Formulation and Lyophilization Development". Baxter Biopharma Solutions. Dec. 13, 2016 [online] [Downloaded from https://www.baxterbiopharmasolutions.com/pdf/whitepapers/ on Nov. 5, 2020] (Year: 2016).*
Carpenter et al. "Rational Design of Stable Lyophilized Protein Formulations: Some Practical Advice". Pharmaceutical Research, vol. 14, No. 8, 1997. (Year: 1997).*

* cited by examiner

*Primary Examiner* — Elly-Gerald Stoica
(74) *Attorney, Agent, or Firm* — Morgan, Lewis & Bockius LLP; Christopher J. Betti

(57) ABSTRACT

The present disclosure relates to a pharmaceutical composition, which comprises an IL-15 protein complex and a citrate buffer solution. In addition, the pharmaceutical composition may also comprise a sugar and a non-ionic surfactant. The pharmaceutical composition in the present disclosure demonstrates a high degree of stability even after being stored at 2-8° C. for several months.

14 Claims, 2 Drawing Sheets
Specification includes a Sequence Listing.

SEQUENCE LISTING

```
<160> NUMBER OF SEQ ID NOS: 2

<210> SEQ ID NO 1
<211> LENGTH: 114
<212> TYPE: PRT
<213> ORGANISM: artificial sequence
<220> FEATURE:
<223> OTHER INFORMATION: IL-15 (L52C)

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Cys Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 2
<211> LENGTH: 315
<212> TYPE: PRT
<213> ORGANISM: artificial sequence
<220> FEATURE:
<223> OTHER INFORMATION: IL-15R alpha-Sushi+(S40C)-Fc

<400> SEQUENCE: 2

Ile Thr Cys Pro Pro Pro Met Ser Val Glu His Ala Asp Ile Trp Val
1               5                   10                  15
```

```
Lys Ser Tyr Ser Leu Tyr Ser Arg Glu Arg Tyr Ile Cys Asn Ser Gly
            20              25                  30

Phe Lys Arg Lys Ala Gly Thr Cys Ser Leu Thr Glu Cys Val Leu Asn
        35              40                  45

Lys Ala Thr Asn Val Ala His Trp Thr Thr Pro Ser Leu Lys Cys Ile
    50              55              60

Arg Asp Pro Ala Leu Val His Gln Arg Gly Gly Gly Ser Gly Gly
65              70              75              80

Gly Gly Ser Glu Pro Lys Ser Ser Asp Lys Thr His Thr Cys Pro Pro
            85              90              95

Cys Pro Ala Pro Glu Leu Leu Gly Gly Pro Ser Val Phe Leu Phe Pro
            100             105             110

Pro Lys Pro Lys Asp Thr Leu Met Ile Ser Arg Thr Pro Glu Val Thr
        115             120             125

Cys Val Val Val Asp Val Ser His Glu Asp Pro Glu Val Lys Phe Asn
    130             135             140

Trp Tyr Val Asp Gly Val Glu Val His Asn Ala Lys Thr Lys Pro Arg
145             150             155             160

Glu Glu Gln Tyr Asn Ser Thr Tyr Arg Val Val Ser Val Leu Thr Val
                165             170             175

Leu His Gln Asp Trp Leu Asn Gly Lys Glu Tyr Lys Cys Lys Val Ser
            180             185             190

Asn Lys Ala Leu Pro Ala Pro Ile Glu Lys Thr Ile Ser Lys Ala Lys
        195             200             205

Gly Gln Pro Arg Glu Pro Gln Val Tyr Thr Leu Pro Pro Ser Arg Glu
    210             215             220

Glu Met Thr Lys Asn Gln Val Ser Leu Thr Cys Leu Val Lys Gly Phe
225             230             235             240

Tyr Pro Ser Asp Ile Ala Val Glu Trp Glu Ser Asn Gly Gln Pro Glu
            245             250             255

Asn Asn Tyr Lys Thr Thr Pro Pro Val Leu Asp Ser Asp Gly Ser Phe
        260             265             270

Phe Leu Tyr Ser Lys Leu Thr Val Asp Lys Ser Arg Trp Gln Gln Gly
        275             280             285

Asn Val Phe Ser Cys Ser Val Met His Glu Ala Leu His Asn His Tyr
    290             295             300

Thr Gln Lys Ser Leu Ser Leu Ser Pro Gly Lys
305             310             315
```

IL-15 PROTEIN COMPLEX PHARMACEUTICAL COMPOSITION

CROSS-REFERENCE TO RELATED APPLICATIONS

This application is the national stage of International Patent Application No. PCT/CN2018/096775, filed Jul. 24, 2018, which claims the benefit of and priority to Chinese Patent Application No. 201710611317.2, filed Jul. 25, 2017, each of which are incorporated herein by reference in their entirety.

FIELD OF THE INVENTION

The invention belongs to the field of pharmaceutical preparations, in particular, it relates to a pharmaceutical composition comprising IL-15 protein complex and its use as a medicament.

BACKGROUND OF THE INVENTION

Interleukin-15 (IL-15) is a cytokine with about 12-14 kD, discovered by Grabstein et al in 1994. It can play a role in normal immune response in vivo, such as promoting proliferation of T cells, B cells, and natural killer cells (NK).

IL-15 is a member of Small Four α-helix Bundle Family of Cytokines. IL-15 exerts biological activity by binding to its receptor. IL-15 receptor consists of three receptor subunits: IL-15 receptor alpha (IL-15Rα), IL-2 receptor beta (IL-2R13, also known as IL-15Rβ or CD122) and γc (also known as CD132). IL-15Rα contains a Sushi domain, which is capable of binding to IL-15 and is essential for the biological function of bound IL-15.

In recent years, it has been found that the biological activity of IL-15 is significantly enhanced once IL-15 binds to its receptor IL-15Rα to form a complex. Studies have shown that the complex formed by IL-15 and its soluble receptor IL-15Rα is significantly superior to IL-15 alone in stimulating the proliferation of memory CD8+T lymphocytes and NT/NKT cells. The IL-15/IL-15Rα complex significantly amplifies and induces the proliferation of $CD12^{high}$ cells, including $CD44^{highCD}8^+$ memory T cells which have been stimulated by antigens. The ability of IL-15/IL-15Rα complex to stimulate the proliferation and maintain the survival of memory $CD8^+$ T cells is 10 times higher than that of IL-15 alone, and the mechanism may be associated with the effect of trans-presentation.

Due to the good expectations of IL-15 in the field of tumor immunotherapy, the NIH first conducted studies on the treatment of tumors with IL-15 and attempted to advance the study toward the clinical phase I study. However, there are some problems about IL-15, for example, due to the small molecular weight and short half-life in vivo, it is difficult to control the repeated administration dose of IL-15, and easy to cause systemically immunological side effects. Therefore, there is an urgent need to improve the half-life of IL-15 in vivo, to promote or to enhance the biological activity thereof in vivo. Many domestic or foreign companies or research institutes were engaged in studies on IL-15 immunotherapy, for example, patent CN100334112C(Shanghai Haixin Biotechnology Co., Ltd.) relates to an IL-15-hIgG4Fc homodimeric protein for use in the treatment of microbial infections. The introduction of disulfide bond between IL-15 and IL-15Rα into the complex molecules of the present application can improve the molecular stability and biological activity, and can also simplify the preparation process.

However, macromolecular protein drugs are not stable, such as being susceptible to degradation, polymerization, or undesired chemical modification, due to their high molecular weight and complex structure. In order to make protein drug suitable for administration, to maintain stability during storage, transportation and subsequent use, and also to exert better effects, studies on stable formulation of protein drugs are particularly important.

Currently, a number of companies have developed IL-15 protein complexes, for example, CN103370339A, CN100334112, CN101735982, WO2007001677, US20070160578, WO2016/095642 and the like. However, for IL-15 protein complexes with new structure, there is still a need to develop a pharmaceutical composition (formulation) comprising the IL-15 protein complex which is more suitable for administration.

SUMMARY OF THE INVENTION

The present invention provides a pharmaceutical composition comprising an IL-15 protein complex and a buffer, wherein the IL-15 protein complex consists of IL-15 and any one selected from the group consisting of:
  IL-15 receptor,
  a fragment comprising an extracellular region of IL-15 receptor, and
  a fusion protein comprising an extracellular region of IL-15 receptor.

The buffer is selected from the group consisting of histidine buffer, succinate buffer, phosphate buffer and citrate buffer, preferably citrate buffer, more preferably citric acid-sodium citrate buffer.

In an alternative embodiment, the concentration of the IL-15 protein complex in the pharmaceutical composition (i.e., the concentration of the IL-15 protein complex formulated in the buffer) is from about 1 mg/ml to 50 mg/ml, preferably from about 1 mg/ml to 20 mg/ml, most preferably from 1 mg/ml to 10 mg/ml. As non-limiting examples, include 1 mg/ml, 2 mg/ml, 3 mg/ml, 4 mg/ml, 5 mg/ml, 6 mg/ml, 7 mg/ml, 8 mg/ml, 9 mg/ml, 10 mg/ml.

In an alternative embodiment, the IL-15 protein complex concentration in the pharmaceutical composition is in the form of small dosage, from about 0.9 mg/ml to 1.1 mg/ml, preferably about 1 mg/ml.

In an alternative embodiment, the concentration of the buffer is from about 5 mM to 30 mM, preferably from about 10 mM to 20 mM, and as non-limiting examples, include 10 mM, 11 mM, 12 mM, 13 mM, 14 mM, 15 mM, 16 mM, 17 mM, 18 mM, 19 mM, 20 mM, more preferably about 10 mM±2 mM, and most preferably 10 mM.

In an alternative embodiment, the pH value of the buffer in the pharmaceutical composition is from about 5.0 to 6.0, preferably from about 5.0 to 5.5, and as non-limiting examples, include about 5.0, about 5.1, about 5.15, about 5.2, about 5.25, about 5.3, about 5.35, about 5.4, about 5.45, about 5.5, more preferably from about 5.15 to 5.25, and most preferably about 5.2.

Further, in an alternative embodiment, the pharmaceutical composition further comprises saccharide. The "saccharide" in the present disclosure comprises conventional composition $(CH_2O)_n$ and derivatives thereof, including monosaccharides, disaccharides, trisaccharides, polysaccharides, sugar alcohols, reducing sugars, non-reducing sugars and the like, which can be selected from the group consisting of glucose, sucrose, trehalose, lactose, fructose, maltose, dextran, glycerol, erythritol, glycerol, arabitol, xylitol, sorbitol, mannitol, melibiose, melezitose, melitriose, mannotriose, stachyose, maltose, lactulose, maltulose, sorbitol, maltitol, lactitol, iso-maltoxose and the like. The preferred saccharide is non-reducing disaccharide, more preferably trehalose or sucrose. In the present disclosure, "trehalose" is preferably α,α-trehalose dihydrate.

In an alternative embodiment, the concentration of the sugar in the pharmaceutical composition is from about 60 mg/ml to about 90 mg/ml, preferably 75 mg/ml±5 mg/ml, non-limiting examples include 70 mg/ml, 71 mg/ml, 72 mg/ml, 73 mg/ml, 73 mg/ml, 74 mg/ml, 75 mg/ml, 76 mg/ml, 77 mg/ml, 78 mg/ml, 79 mg/ml, 80 mg/ml, most preferably 75 mg/ml.

In an alternative embodiment, the pharmaceutical composition further comprises surfactant(s). The surfactant can be selected from the group consisting of polysorbate 20, polysorbate 80, poloxamer, Triton, sodium dodecyl sulfonate, sodium lauryl sulfonate, sodium octyl glycoside, lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauramido propyl-betaine, cocaramide propyl-betaine, oleyamide propyl-betaine, myristylamide propyl-betaine, palmitamide propyl-betaine, isostearamide propyl-betaine, myristylamide propyl-dimethylamine, palmitamide propyl-dimethylamine, isostearamide propyl-dimethylamine, sodium methyl cocoyl, sodium methyl oleyl taurate, polyethylene glycol, polypropylene glycol, copolymer of ethylene and propylene glycol, and the like. Surfactant is preferably polysorbate 80 or polysorbate 20, more preferably polysorbate 20.

In an alternative embodiment, the concentration of the surfactant in the pharmaceutical composition is from about 0.1 mg/ml to 0.6 mg/ml, preferably from about 0.4 mg/ml to 0.6 mg/ml, and non-limiting examples include 0.4 mg/ml, 0.42 mg/ml, 0.44 mg/ml, 0.46 mg/ml, 0.48 mg/ml, 0.5 mg/ml, 0.52 mg/ml, 0.54 mg/ml, 0.56 mg/ml, 0.58 mg/ml, 0.6 mg/ml, most preferably 0.5 mg/ml.

In an alternative embodiment, the pharmaceutical composition comprises:
(a) 1 mg/ml to 10 mg/ml IL-15 protein complex,
(b) 5 mM to 30 mM citrate buffer,
(c) 60 mg/ml to 90 mg/ml trehalose, and
(d) 0.1 mg/ml to 0.6 mg/ml polysorbate 20, the pH of the pharmaceutical composition is about 5.0 to 6.0.

In an alternative embodiment, the pharmaceutical composition comprises: (a) 1 mg/ml to 5 mg/ml IL-15 protein complex, (b) 10 to 20 mM citrate buffer, (c) 60 mg/ml to 90 mg/ml trehalose, and (d) 0.4 mg/ml to 0.6 mg/ml polysorbate 20, the pH of the pharmaceutical composition is about 5.0 to 5.5.

In an alternative embodiment, the pharmaceutical composition comprises:
(a) 1 mg/ml IL-15 protein complex,
(b) 10 mM±2 mM citrate buffer,
(c) 75 mg/ml±5 mg/ml trehalose, and
(d) 0.4 mg/ml to 0.6 mg/ml polysorbate 20, the pH of the pharmaceutical composition is about 5.15 to 5.25.

In an alternative embodiment, the pharmaceutical composition comprises:
(a) 1 mg/ml IL-15 protein complex,
(b) 10 mM citrate buffer,
(c) 75 mg/ml trehalose, and
(d) 0.5 mg/ml polysorbate 20, the pH of the pharmaceutical composition is about 5.15 to 5.25, preferably pH 5.2.

In an alternative embodiment, the pharmaceutical composition comprises: (a) 1 mg/ml IL-15 protein complex 3, and (b) 10 mM citrate buffer, the pH of the pharmaceutical composition is about 5.0 to 5.5.

In an alternative embodiment, the pharmaceutical composition comprises: (a) 1 to 5 mg/ml IL-15 protein complex 3, (b) 10 mM citric acid-sodium citrate buffer, (c) 60 mg/ml sucrose, and (d) 0.4 mg/ml polysorbate 20, the pH of the pharmaceutical composition is about 5.5.

In an alternative embodiment, the pharmaceutical composition comprises: (a) 1 mg/ml IL-15 protein complex 3, (b) 10 mM citric acid-sodium citrate buffer, and (c) 60 mg/ml trehalose, the pH of the pharmaceutical composition is about 5.5.

In an alternative embodiment, the pharmaceutical composition comprises: (a) 1 mg/ml IL-15 protein complex 3, (b) 10 mM citric acid-sodium citrate buffer, and (c) 90 mg/ml trehalose, the pH of the pharmaceutical composition is about 5.5.

In an alternative embodiment, the pharmaceutical composition comprises: (a) 1 mg/ml IL-15 protein complex 3, (b) 10 mM±2 mM citric acid-sodium citrate buffer, (c) 75 mg/ml±5 mg/ml trehalose, and (d) 0.4 mg/ml to 0.6 mg/ml polysorbate 20, the pH of the pharmaceutical composition is about 5.15 to 5.25.

In an alternative embodiment, the pharmaceutical composition comprises: (a) 1 mg/ml IL-15 protein complex 3, (b) 10 mM±2 mM citric acid-sodium citrate buffer, (c) 75 mg/ml±5 mg/ml trehalose, and (d) 0.4 mg/ml to 0.6 mg/ml polysorbate 20, the pH of the pharmaceutical composition is about 5.15 to 5.25.

In an alternative embodiment, the pharmaceutical composition comprises: (a) 1 mg/ml IL-15 protein complex, (b) 10 mM citric acid-sodium citrate buffer, (c) 75 mg/ml trehalose, and (d) 0.5 mg/ml polysorbate 20, the pH of the pharmaceutical composition is about 5.2.

In an alternative embodiment, the IL-15 protein complex comprised in the pharmaceutical composition consists of IL-15 having at least 95%, 96%, 97%, 98%, 99% or 100% sequence identity to the polypeptide of SEQ ID NO: 1 and a fusion protein of IL-15 receptor having at least 95%, 96%, 97%, 98%, 99% or 100% sequence identity to the polypeptide of SEQ ID NO: 2.

In a preferred embodiment, the IL-15 protein complex consists of IL-15 of SEQ ID NO: 1 and a fusion protein of IL-15 receptor of SEQ ID NO: 2.

In some embodiments, the pharmaceutical composition is stable at 2-8° C. for at least 3 months, at least 6 months, at least 12 months, at least 18 months, or at least 24 months. In some embodiments, the pharmaceutical composition is stable at 40° C. for at least 7 days, at least 14 days or at least 28 days.

The present invention also provides a method of preparing the pharmaceutical composition described above, including preparing the pharmaceutical composition with IL-15 protein complex and a buffer. In the pharmaceutical composition, the concentration of the IL-15 protein complex is from about 1 mg/ml to 10 mg/ml, preferably from about 1 mg/ml to 5 mg/ml, and most preferably from about 0.9 mg/ml to 1.1 mg/ml, more preferably 1 mg/ml.

The buffer is preferably citrate buffer, the concentration of the buffer is preferably from about 5 mM to 30 mM, more preferably from about 5 mM to 20 mM, most preferably about 10 mM±2 mM, and the pH of the buffer is about 5.0 to 6.0, the pH is preferably from about 5.0 to 5.5, most preferably from about 5.15 to 5.25. The pH of the buffer with which the pharmaceutical composition is prepared in the present disclosure is substantially the same as the final pH of the pharmaceutical composition.

The IL-15 protein complex consists of IL-15 and any one selected from the group consisting of:
IL-15 receptor,
a fragment comprising an extracellular region of IL-15 receptor, and
a fusion protein comprising an extracellular region of IL-15 receptor.

Specifically, the IL-15 protein complex consists of IL-15 having at least 95% sequence identity to the polypeptide of SEQ ID NO: 1 and a fusion protein of IL-15 receptor having at least 95% sequence identity to the polypeptide of SEQ ID NO: 2.

Preferably, the IL-15 protein complex consists of IL-15 of SEQ ID NO: 1 and a fusion protein of IL-15 receptor of SEQ ID NO: 2.

In an alternative embodiment, the method of preparing the pharmaceutical composition described above further comprises the step of adding trehalose and polysorbate 20, preferably the concentration of the trehalose is from about 60 mg/ml to 90 mg/ml, preferably 75±5 mg/ml, most preferably 75 mg/ml, the concentration of the polysorbate 20 is from about 0.1 mg/ml to 0.6 mg/ml, preferably from about 0.4 mg/ml to 0.6 mg/ml, most preferably about 0.5 mg/ml.

The present invention also provides a method of preparing a lyophilized formulation comprising the IL-15 protein complex, which comprises the step of lyophilizing the pharmaceutical composition described above.

In an alternative embodiment, the step of lyophilization included in the method of preparing a lyophilized formulation comprising the IL-15 protein complex comprises the steps of pre-freezing, primary drying and secondary drying, successively. The step of lyophilization is carried out by freezing the formulation and subsequently sublimating the water at a temperature suitable for primary drying. Under such conditions, the product temperature is lower than the eutectic point or the decomposition temperature of the formulation. Under a suitable pressure, typically in the range of about 50-250 mTorr, the temperature range for primary drying is typically from about −30 to 25° C. (assuming that the product remains frozen during the primary drying). The time required for drying is dependent on the size and type of the formulation, container (e.g., glass vial) containing the sample, and the volume of the liquid. The time may range from a few hours to a few days (e.g., 40-60 hours). The secondary drying can be carried out at about 0-40° C., which is mainly dependent on the type and size of the container and the type of protein employed. Time for the secondary drying is determined by the desired residual moisture level in the product and typically at least about 5 hours is required. Typically, the formulation lyophilized under low pressure has a water content of less than about 5%, preferably less than about 3%. The pressure may be the same as the pressure applied in the step of primary drying. Preferably, the pressure applied during the secondary drying is lower than that during the primary drying. Conditions for lyophilization may vary with the sizes of the formulation and the vial. The pre-freezing of the present disclosure means freezing from 5° C. to −40° C. or to −50° C., preferably −45° C., regardless of the vacuum degree. The temperature for the primary drying is preferably −25° C.; the vacuum degree is from 0.01 mBar to 0.2 mBar, and is most preferably 0.08 mBar. The temperature for the secondary drying is from 20° C. to 30° C., most preferably 25° C., and the vacuum degree is from 0.01 mBar to 0.2 mBar, most preferably 0.08 mBar, reduced to 0.005 mBar-0.02 mBar, most preferably 0.01 mBar.

The present disclosure also provides a lyophilized formulation comprising the IL-15 protein complex prepared by the method of preparing a lyophilized formulation comprising the IL-15 protein complex described above.

The present disclosure also provides a method of preparing a reconstituted solution of the lyophilized formulation comprising the pharmaceutical composition described above, including a step of reconstituting the lyophilized formulation described above, wherein the solvent used for reconstitution is preferably water for injection.

The present invention also provides a reconstituted solution comprising the IL-15 protein complex prepared by the method of preparing a reconstituted solution described above.

In an alternative embodiment, in the reconstituted solution, the concentration of the IL-15 protein complex is from about 0.9 mg/ml to 1.1 mg/ml, preferably about 1 mg/ml.

In an alternative embodiment, in the reconstituted solution, the pharmaceutical composition has pH of from about 5.0 to 6.0, preferably from about 5.0 to 5.5, more preferably from about 5.15 to 5.25, most preferably 5.2.

In an alternative embodiment, the reconstituted solution comprises citric acid-sodium citrate buffer, and the concentration of the buffer is from about 5 mM to 30 mM, preferably from about 10 mM to 20 mM, more preferably 10 mM.

In an alternative embodiment, the reconstituted solution further comprises disaccharide, preferably the disaccharide is selected from the group consisting of trehalose and sucrose, most preferably trehalose.

In an alternative embodiment, in the reconstituted solution, the concentration of the sugar is from about 60 mg/ml to 90 mg/ml, preferably about 75±5 mg/ml, more preferably 75 mg/ml.

In an alternative embodiment, the reconstituted solution further comprises a surfactant, the surfactant is preferably polysorbate, more preferably is polysorbate 20.

In an alternative embodiment, in the reconstituted solution, the concentration of the surfactant is from about 0.1 mg/ml to 0.6 mg/ml, preferably from about 0.4 mg/ml to 0.6 mg/ml, most preferably 0.5 mg/ml.

The present disclosure also relates to a lyophilized formulation comprising IL-15 protein complex, and the lyophilized formulation is reconstituted to form the pharmaceutical composition described above.

The disclosure further provides a product or kit comprising a container containing any pharmaceutical composition described herein. In some embodiments, the glass vial is a vial for injection made of neutral borosilicate glass.

The disclosure further provides a use of the pharmaceutical composition or lyophilized formulation or reconstituted solution of the lyophilized formulation described above in the manufacture of a medicament for the treatment of IL-15 related diseases or conditions.

In an alternative embodiment, the disease or condition described in the use described above is selected from the group consisting of infectious disease, cancer, blood disease, inflammatory disease, and autoimmune disease; the cancer is preferably selected from the group consisting of melanoma, colorectal cancer, skin cancer, lymphoma, renal cell carcinoma, liver cancer, lung cancer, stomach cancer, breast cancer; the infectious disease is preferably selected from the group consisting of variola virus infection, HIV infection, bacterial infection, fungal infection and HBV infection; the blood disease is preferably selected from the group consisting of anemia, acute myeloid leukemia, myelodysplastic syndrome and T-cell large granular lymphocytic leukemia; the autoimmune disease is preferably selected from the group consisting of multiple sclerosis, psoriasis, rheumatoid arthritis, gastritis and mucositis.

In an alternative embodiment, according to the above use, wherein the pharmaceutical composition or the lyophilized formulation or the reconstituted solution of the lyophilized formulation is administered in combination with a small molecule inhibitor or an antibody drug; the small molecule inhibitor is preferably a targeting chemotherapeutic drug or a radiotherapeutic drug, more preferably an alkylating agent; the antibody drug is preferably a monoclonal antibody drug, more preferably anti-CD20, anti-PD1, anti-PDL1, anti-Her2, anti-EGFR, anti-c-MET antibody.

The present disclosure also provides a use of the pharmaceutical composition or lyophilized formulation or reconstituted solution of the lyophilized formulation described above in the preparation of a medicament for cellular immunotherapy, in particular, the cellular immunotherapy is the immunotherapy for tumor cells, such as DC (Dendritic Cell Immunotherapy), CIK (Cytokine Induced Killer Cell Immunotherapy), DC-CIK (Dendritic Cell-Cytokine Induced Killer Cell Immunotherapy), ECIK (Enhanced Cytokine Induced Killer Cell Immunotherapy), NK (Natural Killer Cell Immunotherapy), CAS-T (Combined Antigen Stimulated T Cell Immunotherapy), BiAb-T (Bispecific antigen binding T cell immunotherapy), TCR-T (T cell receptor engineered T-Cell Immunotherapy), CAR-T (Chimeric Antigen Receptor T-Cell Immunotherapy).

The disclosure further provides a method of treating IL-15 related diseases or conditions comprising a step of administering to a subject the pharmaceutical composition or lyophilized formulation or reconstituted solution of the lyophilized formulation described above.

In an alternative embodiment, the method of treating IL-15 related diseases or conditions described above, wherein the disease or condition is selected from the group consisting of infectious disease, cancer, blood disease, inflammatory disease, and autoimmune disease.

The cancer is preferably selected from the group consisting of melanoma, colorectal cancer, skin cancer, lymphoma, renal cell carcinoma, liver cancer, lung cancer, stomach cancer and breast cancer; the infectious disease is preferably selected from the group consisting of variola virus infection, HIV infection, bacterial infection, fungal infection and HBV infection; the blood disease is preferably selected from the group consisting of anemia, acute myeloid leukemia, myelodysplastic syndrome and T-cell large granular lymphocytic leukemia; the autoimmune disease is preferably selected from the group consisting of multiple sclerosis, psoriasis, rheumatism arthritis, gastritis and mucositis.

In an alternative embodiment, the aforementioned method of treating IL-15 related diseases or conditions, wherein the pharmaceutical composition or the lyophilized formulation or the reconstituted solution of the lyophilized formulation is administered in combination with a small molecule inhibitor or with an antibody drug; the small molecule inhibitor is preferably a targeting chemotherapeutic drug or a radiotherapeutic drug, more preferably an alkylating agent; the antibody drug is preferably a monoclonal antibody drug, more preferably anti-CD20, anti-PD1, anti-PDL1, anti-Her2, anti-EGFR, anti-c-MET antibody.

It is to be understood that one, some, or all of the features of the various embodiments described herein may be combined to form other embodiments of the disclosure. These and other aspects of the disclosure will be apparent to those skilled in the art. These and other embodiments of the disclosure are further described by the following detailed description.

DETAILED DESCRIPTION OF THE DISCLOSURE

I. Terms

Figure 1:
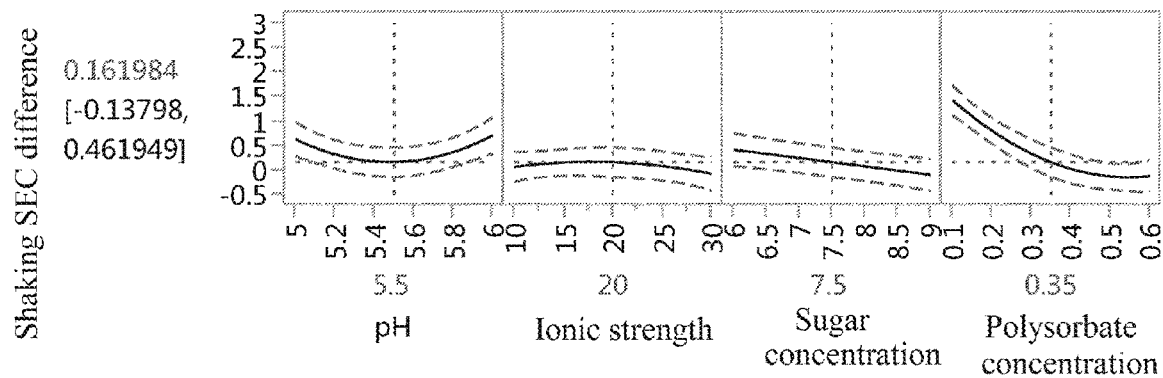
FIG. 1 is a fitting curve chart indicating the difference in purity values of SEC after shaking when compared with that at D0.

In order to more easily understand the present disclosure, certain technical and scientific terms are specifically defined below. All other technical and scientific terms used herein have the meaning commonly understood by one of ordinary skill in the art to which this disclosure belongs, unless otherwise explicitly defined herein.

"Buffer" refers to a buffer that is resistant to changes in pH by the action of its acid-base conjugate components. Examples of the buffer which controls the pH within an appropriate range include acetate, succinate, gluconate, histidine, oxalate, lactate, phosphate, citrate, tartrate, fumarate, glycylglycine and other organic acid buffers.

"Histidine buffer" is a buffer containing histidine ions. Examples of the histidine buffer include histidine-hydrochloride, histidine-acetate, histidine-phosphate, histidine-sulfate buffer, and the like, and histidine-hydrochloride buffer is preferred. The histidine-hydrochloride buffer is prepared by histidine and hydrochloric acid, or by histidine and histidine hydrochloride. "Citrate buffer" is a buffer that includes citrate ions. Examples of the citrate buffer include citric acid-sodium citrate, citric acid-histidine, citric acid-potassium citrate, citric acid-calcium citrate, citric acid-magnesium citrate, and the like. A preferred citrate buffer is citric acid-sodium citrate buffer.

"Succinate buffer" is a buffer comprising succinate ions. Examples of the succinate buffer include succinic acid-sodium succinate, histidine succinate, succinic acid-potassium succinate, succinic acid-calcium succinate, and the like. A preferred succinate buffer is succinic acid-sodium succinate buffer.

"Phosphate buffer" is a buffer comprising phosphate ions. Examples of the phosphate buffer include disodium hydrogen phosphate-sodium dihydrogen phosphate, disodium hydrogen phosphate-potassium dihydrogen phosphate, and the like. A preferred phosphate buffer is disodium hydrogen phosphate-sodium dihydrogen phosphate buffer.

"Acetate buffer" is a buffer comprising acetate ions. Examples of the acetate buffer include acetic acid-sodium acetate, acetate histidine, acetic acid-potassium acetate, acetic acid-calcium acetate, acetic acid-magnesium acetate, and the like. A preferred acetate buffer is acetic acid-sodium acetate buffer.

"Trehalose" is also known as "α,α-trehalose dihydrate".

"Pharmaceutical composition" means a mixture comprising one or more of the IL-15 protein complexes described herein and other chemical components, such as physiological/pharmaceutically acceptable carriers and excipients. The purpose of the pharmaceutical composition is to facilitate the stable storage, transportation and to promote the administration to the organism, so as to facilitate the absorption and the biological activity of the active ingredient. As used herein, "pharmaceutical composition" and "formulation" are not mutually exclusive.

According to the present disclosure, the solvent of the solution form of the pharmaceutical composition is water, unless otherwise specified.

"Lyophilized formulation" means a formulation or a pharmaceutical composition obtained by vacuum lyophilization of pharmaceutical composition or a formulation in liquid or solution form.

The pharmaceutical composition of the present disclosure is capable of achieving a stable effect: the protein complex included in the pharmaceutical composition substantially retains its physical stability and/or chemical stability and/or biological activity during storage. Preferably, the pharmaceutical composition substantially retains its physical stability and chemical stability as well as biological activity during storage. The length for storage is generally selected based on the predetermined shelf life of the pharmaceutical composition. There are currently a number of analytical techniques for measuring the stability of protein, which can be used to measure the stability after being stored for a selected period of time at a selected temperature.

A stable protein pharmaceutical formulation is a formulation in which no significant change is observed under the following conditions: being stored at a cool temperature (2-8° C.) for at least 3 months, preferably 6 months, more preferably 1 year, and even more preferably up to 2 years. In addition, stable liquid formulations include those exhibit desirable characteristics after being stored at temperature of 25° C. to 40° C. for 1 month, 3 months or 6 months. Typically, acceptable criteria for stability are as follows: typically no more than about 10%, preferably no more than about 5% of the protein complex monomers are degraded, as measured by SEC-HPLC; By visual inspection, the pharmaceutical formulation is colorless or from clear to slightly milky white; No more than ±10% variation occurs in the concentration, pH and osmolality of the formulation; Generally no more than about 10%, preferably no more than about 5% truncation is observed; Generally no more than about 10%, preferably no more than about 5% aggregates are formed.

A protein complex is deemed to "retain its physical stability" in the pharmaceutical formulation, when said protein complex does not show a significant increase in aggregation, precipitation and/or denaturation, by visual inspection of the color and/or clarity, or by being measured via UV light scattering, size exclusion chromatography (SEC) and dynamic light scattering (DLS). Changes in protein conformation can be assessed by fluorescence spectroscopy, which determines the tertiary structure of the protein, and by FTIR spectroscopy, which determines the secondary structure of the protein.

A protein complex is deemed to "retain its chemical stability" in the pharmaceutical formulation, when said protein complex does not show a significant chemical modification. Chemical stability can be assessed by detecting and quantifying chemically altered forms of the protein. Degradation processes that frequently alter the chemical structure of a protein include hydrolysis or truncation (assessed by methods such as size exclusion chromatography and SDS-PAGE), oxidation (assessed by methods such as peptide spectroscopy in combination with mass spectrometry or MALDI/TOF/MS), deamidation (assessed by methods such as ion exchange chromatography, capillary isoelectric focusing, peptide spectroscopy, isoaspartic acid measurement) and isomerization (assessed by measuring for example the content of isoaspartic acid, peptide spectroscopy).

A protein complex is deemed to "retain its biological activity" in the pharmaceutical formulation, when the biological activity of the protein complex at a given time is still within the predetermined range of biological activity exhibited at the time when the pharmaceutical formulation was initially prepared. The biological activity of the protein complex can be determined, for example, by antigen binding assay.

The three-letter code and the one-letter code for amino acids used in the present disclosure are described in J. biol. chem, 243, p3558 (1968).

"IL-15 protein complex" is a protein complex formed by IL-15 protein and IL-15 receptor (and protein containing IL-15 receptor functional fragment), wherein IL-15 receptor functional fragment includes a fragment containing IL-15 receptor extracellular region or a fusion protein containing IL-15 receptor extracellular region. "IL-15 protein complex 3" refers to protein complex 3 described in WO2016/095642, which is a protein complex formed by mutated IL-15 (L52C) bound to IL-15Rα-Sushi+(S40C)-Fc, wherein IL-15 has L52C mutation, IL-15Rα extracellular region has S40C mutation (IL-15Rα-Sushi), and IL-15Rα-Sushi+(S40C) is fused to Fc.

```
Wherein, IL-15(L52C) (SEQ ID NO: 1):
NWVNVISDLKKIEDLIQSMHIDATLYTESDVHPSCKVTAMKCFLLEL

QVISCESGDASIHDTVENLILANNSLSSNGNVTESGCKECEELEEKN

IKEFLQSFVHIVQMFINTS

IL-15Rα-Sushi+(S40C)-Fc (SEQ ID NO: 2):
ITCPPPMSVEHADIWVKSYSLYSRERYICNSGFKRKAGTCSLTECVL

NKATNVAHWTTPSLKCIRDPALVHQRGGGGSGGGGSEPKSSDKTHTC

PPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYK

CKVSNKALPAPIEKTISKAKGQPREPQVYTLPPSREEMTKNQVSLTC

LVKGFYPSDIAVEWESNGQPENNYKTTPPVLDSDGSFFLYSKLTVDK

SRWQQGNVFSCSVMHEALHNHYTQKSLSLSPGK
```

Methods for producing and purifying proteins are well known in the art, such as the Molecular Cloning: a laboratory manual, Cold Spring Harbor Laboratory Press, Chapters 5-8 and 15. The protein complex of the disclosure is produced by conventional genetic engineering methods.

The engineered protein complex of the present disclosure can be prepared and purified by conventional methods. For example, cDNA sequence encoding IL-15 and IL-15 receptor can be cloned and recombined into GS expression vector. The recombinant protein expression vector can be stably transfected into CHO cells. As a recommended prior art, mammalian expression systems may result in glycosylation of proteins, particularly at the highly conserved N-terminal site of the Fc region. Stable clones may be obtained by expressing proteins that specifically bind to human IL-15. Positive clones are expanded in serum-free medium in a bioreactor to produce protein complex. The culture medium into which the protein is secreted can be purified by a conventional technique. For example, purification is carried out by using A or G Sepharose FF column containing adjusted buffer. The non-specifically bound components are washed away. The bound protein complex is eluted by a pH gradient, and the protein fraction is detected by SDS-PAGE and collected. The protein complex can be concentrated by filtration with a conventional method. Soluble mixtures and multimers can also be removed by conventional methods such as molecular sieves, ion exchange. The resulting product needs to be frozen immediately, such as at −70° C., or lyophilized.

Amino acid sequence "identity" refers to sequence similarity between two proteins or polypeptides. When the positions in two sequences to be compared are occupied by the same amino acid residue, for example if the positions in two polypeptides are occupied by the same amino acid residue, the molecules are deemed to be identical at that position. Examples of algorithms suitable for determining percent sequence identity and percent sequence similarity are BLAST and BLAST 2.0 algorithms, which are described in Altschul et al. (1990) J. Mol. Biol. 215:403-410 and Altschul et al. (1977) Nucleic Acids Res. 25:3389-3402, respectively. Softwares for performing BLAST analyses are publicly available at the National Center for Biotechnology Information (ncbi.nlm.nih.gov).

"Administration" and "treatment", when applied to animal, human, experimental subject, cell, tissue, organ or biological fluid, refers to contacting an exogenous drug, therapeutic agent, diagnostic agent or composition with the animal, human, subject, cell, tissue, organ or biological fluid. "Administration" and "treatment" may refer to, for example, therapeutic, pharmacokinetic, diagnostic, research and experimental methods. Treatment of cells includes contacting the reagents with the cells, and contacting the reagents with the fluid, wherein the fluids are in contact with the cells. "Administration" and "treatment" also mean treating, for example, cells in vitro and ex vivo with reagents, diagnostics, binding compositions, or with another cell. "Treatment", when applied to human, veterinary or research subject, refers to therapeutic treatment, prophylactic or preventive measures, research and diagnostic applications.

"Treatment" means administration of a therapeutic agent to a patient for internal or external use, for example a composition comprising any of the binding compounds of the present disclosure, the patient has one or more symptoms of the disease, and the therapeutic agent is known to have therapeutic effect on these symptoms. Generally, a therapeutic agent is administered to a subject or population to be treated in an amount to effectively alleviate one or more symptoms of the disease, so as to induce the degeneration of symptoms or inhibition the progression of such symptoms to any clinically measurable extent. The amount of therapeutic agent to effectively alleviate the symptom of any particular disease (also referred to as "therapeutically effective amount") can vary depending on a variety of factors, such as the patient's disease state, age and weight, and the ability of the drug to produce a desired effect in the patient. Any clinical test method commonly used by a physician or other professional health care provider to assess the severity or progression of the conditions can be used to assess whether the symptoms of a disease have been alleviated. While the embodiments of the disclosure (e.g., methods of treatment or product) may be ineffective in ameliorating the symptoms of single target disease, they should alleviate the symptoms of the target disease in a statistically significant number of patients according to any statistical test known in the art, such as Student's t-test, chi-square test, Mann and Whitney U-test, Kruskal-Wallis test (H test), Jonckheere-Terpstra test, and Wilcoxon test.

An "effective amount" includes an amount sufficient to ameliorate or prevent symptoms or conditions of a medical disease. An effective amount also means an amount sufficient to allow or facilitate the diagnosis. The effective amount for a particular patient or veterinary subject can vary depending on factors such as the condition to be treated, the overall health of the patient, the method, route and dosage of the administration, and the severity of the side effects. An effective amount may be the maximum dosage or dosing regimen that avoids significant side effects or toxic effects.

II. Examples and Test Examples

The disclosure is further described in the following examples. However, these examples are not intended to limit the scope of the disclosure.

Experimental methods, for which the specific conditions are not specifically indicated in the examples or test examples of the present disclosure, were generally carried out according to conventional conditions or according to the conditions recommended by the manufacturers. See J. Sambrook et al., Molecular cloning: a laboratory manual. Cold Spring Harbor Laboratory Press; Frederick M. Ausubel, The Modern Molecular Biology Method, Greene Press Association. Reagents, for which the source is not specifically indicated, were routinely purchased from the market.

Process for Preparing a Pharmaceutical Composition (Formulation) Comprising the IL-15 Protein Complex

EXAMPLES

The process for preparing a pharmaceutical composition (formulation) comprising the IL-15 protein complex is as follows (the components and compositions of each formulation can be selected and adjusted based on the stability of the protein complex):

The first step: preparing a stock solution comprising IL-15 protein complex 3 (For preparation, expression and purification of IL-15 protein complex 3, see patent application WO2016/095642 filed on Nov. 17, 2015, with application number of PCT/CN2015/094780, which is entirely incorporated herein by reference) and stabilizer components, filtering and then sampling the solution for sterility test. The stock solution was passed through a 0.22 μm PVDF filter and the filtrate was collected.

IL-15 protein complex 3 consists of the following polypeptides:

IL-15(L52C) (SEQ ID NO: 1):
NWVNVISDLKKIEDLIQSMHIDATLYTESDVHPSCKVTAMKCFLLEL

QVISCESGDASIHDTVENLIILANNSLSSNGNVTESGCKECEELEEK

NIKEFLQSFVHIVQMFINTS

IL-15Rα-Sushi+(S40C)-Fc (SEQ ID NO: 2):
ITCPPPMSVEHADIWVKSYSLYSRERYICNSGFKRKAGTCSLTECVL

NKATNVAHWTTPSLKCIRDPALVHQRGGGGSGGGGSEPKSSDKTHTC

PPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYK

CKVSNKALPAPIEKTISKAKGQPREPQVYTLPPSREEMTKNQVSLTC

LVKGFYPSDIAVEWESNGQPENNYKTTPPVLDSDGSFFLYSKLTVDK

SRWQQGNVFSCSVMHEALHNHYTQKSLSLSPGK

The second step: adjusting the loading volume to 1.1 ml, the filtrate was filled in a 2 ml vial, with a stopper plugged incompletely. Samplings are performed at the beginning, the middle and the end of the filling, respectively to monitor the loading difference.

The third step: the liquid solution with a stopper was filled into a lyophilization chamber and lyophilized. The lyophilization includes steps of pre-freezing, primary drying and secondary drying, successively. When the procedure of lyophilization is finished, the stopper is plugged completely under vacuum.

The fourth step: capping with an aluminum cap by using a capping machine.

The fifth step: Visual inspection was performed to confirm the product absence of collapse, accurate of loading volume and other defects. The label of vial was printed and pasted onto the vial. The vials were placed into a paper tray, print and pasting a label onto the paper tray.

Example 1

Formulations of the IL-15 protein complex 3, at a concentration of 1 mg/mL, were prepared in a series of buffers of pH 5.0-8.5. Each formulation was filtered and filled into a 2 mL vial at 1 mL/vial, plugged with a stopper, capped and sealed. The samples were subjected to forced degradation testing, such as by placing at 40° C. high temperature, repeated freezing-thawing and shaking. Appearance and SEC were used as evaluation indexes. The results showed that the purity of SEC monomer in each buffer system was decreased significantly after forced degradation testing at 40° C. However, the decrease in the citrate system was the least. After shaking, freezing-thawing, the SEC in each buffer system (except phosphate system) showed no significant change when compared with that on D0. Hence, citrate was selected as buffer system. For citrate system, at pH 6.0, appearance after freezing-thawing and SEC at 40° C. were slightly worse. Hence, the conditions at pH 5.0 to 5.5 were better.

TABLE 1

Results of Screening Buffer System-pH for IL-15 Protein Complex 3

| Batch Number, type and pH of buffer | Conditions | times | appearance | SEC (%) polymer | monomer | fragment |
|---|---|---|---|---|---|---|
| 1 | N/A | 0 | clear | 0.3 | 96.7 | 3.0 |
| 10 mM buffer pH 5.0 | 40° C. | 17 days | clear | 0.2 | 90.1 | 9.7 |
|  | freezing-thawing | 5 times | clear | 0.4 | 96.7 | 2.9 |
|  | shaking(25° C. 250 rpm) | 2 days | clear | 0.2 | 96.7 | 3.1 |
| 2 | N/A | 0 | clear | 0.5 | 96.7 | 2.8 |
| 10 mM succinate buffer pH 5.5 | 40° C. | 17 days | clear | 0.4 | 88.0 | 11.6 |
|  | freezing-thawing | 5 times | Small and suspended particles | 0.5 | 96.6 | 2.9 |
|  | shaking(25° C. 250 rpm) | 2 days | clear | 0.3 | 96.6 | 3.1 |
| 3 | N/A | 0 | clear | 0.6 | 96.4 | 3.1 |
| 10 mM succinate buffer pH 6.0 | 40° C. | 17 days | clear | 0.4 | 90.1 | 9.5 |
|  | freezing-thawing | 5 times | clear | 0.6 | 96.4 | 3.0 |
|  | shaking(25° C. 250 rpm) | 2 days | clear | 0.3 | 96.8 | 2.9 |
| 4 |  | 0 | clear | 0.5 | 96.9 | 2.6 |
| 10 mM citrate buffer pH 5.0 | 40° C. | 17 days | clear | 0.4 | 93.3 | 6.3 |
|  | freezing-thawing | 5 times | clear | 0.6 | 96.4 | 3.1 |
|  | shaking(25° C. 250 rpm) | 2 days | clear | 0.3 | 96.7 | 3.0 |
| 5 | N/A | 0 | clear | 0.6 | 96.4 | 3.0 |
| 10 mM citrate buffer pH 5.5 | 40° C. | 17 days | clear | 0.3 | 93.9 | 5.8 |
|  | freezing-thawing | 5 times | clear | 0.6 | 96.5 | 2.9 |
|  | shaking(25° C. 250 rpm) | 2 days | clear | 0.4 | 96.6 | 3.1 |
| 6 | N/A | 0 | clear | 0.6 | 96.3 | 3.2 |
| 10 mM citrate buffer pH 6.0 | 40° C. | 17 days | clear | 0.3 | 92.5 | 7.1 |
|  | freezing-thawing | 5 times | Small and suspended particles | 0.6 | 96.7 | 2.7 |
|  | shaking(25° C. 250 rpm) | 2 days | clear | 0.4 | 96.6 | 3.0 |
| 7 | N/A | 0 | clear | 0.5 | 96.9 | 2.6 |
| 10 mM phosphate buffer pH 6.0 | 40° C. | 17 days | clear | 0.3 | 89.4 | 10.3 |
|  | freezing-thawing | 5 times | clear | 0.6 | 96.4 | 2.9 |
|  | shaking(25° C. 250 rpm) | 2 days | Small particles | 0.3 | 97.0 | 2.7 |
| 8 | N/A | 0 | clear | 0.6 | 95.9 | 3.5 |
| 10 mM phosphate buffer pH 7.0 | 40° C. | 17 days | clear | N/A | N/A | N/A |
|  | freezing-thawing | 5 times | clear | 0.7 | 96.1 | 3.2 |
|  | shaking(25° C. 250 rpm) | 2 days | clear | 0.6 | 95.2 | 4.2 |

TABLE 1-continued

Results of Screening Buffer System-pH for IL-15 Protein Complex 3

| Batch Number, type and pH of buffer | Conditions | times | appearance | SEC (%) polymer | monomer | fragment |
|---|---|---|---|---|---|---|
| 9 | N/A | 0 | clear | 0.6 | 96.0 | 3.5 |
| 10 mM phosphate buffer pH 7.5 | 40° C. | 17 days | clear | N/A | N/A | N/A |
| | freezing-thawing | 5 times | clear | 1.5 | 94.5 | 3.9 |
| | shaking(25° C. 250 rpm) | 2 days | clear | 0.5 | 92.8 | 6.6 |
| 10 | N/A | 0 | clear | 0.6 | 95.2 | 4.2 |
| 10 mM phosphate buffer pH 8.0 | 40° C. | 17 days | clear | N/A | N/A | N/A |
| | freezing-thawing | 5 times | clear | 1.4 | 94.6 | 4.0 |
| | shaking(25° C. 250 rpm) | 2 days | clear | 0.5 | 90.1 | 9.4 |
| 11 | N/A | 0 | clear | 0.6 | 95.0 | 4.4 |
| 10 mM phosphate buffer pH 8.5 | 40° C. | 17 days | clear | N/A | N/A | N/A |
| | freezing-thawing | 5 times | clear | 1.1 | 94.8 | 4.1 |
| | shaking(25° C. 250 rpm) | 2 days | clear | 0.5 | 90.5 | 9.0 |
| 12 | N/A | 0 | clear | 0.3 | 96.8 | 2.9 |
| 10 mM Histidine buffer pH 5.5 | 40° C. | 17 days | clear | 0.2 | 90.8 | 9.0 |
| | freezing-thawing | 5 times | clear | 0.4 | 96.2 | 3.4 |
| | shaking(25° C. 250 rpm) | 2 days | clear | 0.2 | 97.0 | 2.8 |
| 13 | N/A | 0 | clear | 0.4 | 97.0 | 2.6 |
| 10 mM Histidine buffer pH 6.0 | 40° C. | 17 days | clear | 0.4 | 92.1 | 7.5 |
| | freezing-thawing | 5 times | clear | 0.4 | 97.1 | 2.5 |
| | shaking(25° C. 250 rpm) | 2 days | clear | 0.3 | 97.0 | 2.7 |

Note:
N/A means no special operation.

Example 2

Formulations comprising IL-15 protein complex 3 at a concentration of 1 mg/mL, 10 mM citric acid-sodium citrate, 60 mg/mL sucrose, pH 5.5 were prepared in buffers containing various concentrations of surfactant as follows:
1) 0.2 mg/mL polysorbate 20
2) 0.4 mg/mL polysorbate 20
3) 0.2 mg/mL polysorbate 80
4) 0.4 mg/mL polysorbate 80

Each formulation was filtered and filled into a 2 mL vial at 1 mL/vial, plugged with a stopper, capped and sealed. The samples were subjected to forced degradation testing, such as by placing at 40° C. high temperature and repeated freezing-thawing. The stability results showed that there was no significant difference in appearance and SEC among different formulations. The results obtained under the condition of 40° C. high temperature and freezing-thawing non-reduced CE-SDS showed that the stability in 0.4 mg/mL polysorbate 20 group is more superior.

TABLE 2

Results of screening Tween for stability of IL-15 protein complex 3

| Type and concentration of Tween | Experimental conditions | SEC (%) polymer | monomer | fragment | Non-reduced CE-SDS (%) | appearance |
|---|---|---|---|---|---|---|
| 0.2 mg/ml polysorbate 20 | 0 | 0.1 | 97.8 | 2.0 | 87.3 | clear |
| | freezing-thawing 5 times | 0.1 | 96.8 | 3.1 | 87.8 | extremely small particles |
| | 40° C. for 14 days | 0.1 | 95.5 | 4.3 | 81.1 | clear |
| 0.4 mg/ml polysorbate 20 | 0 | 0.2 | 97.4 | 2.5 | 86.4 | clear |
| | freezing-thawing 5 times | 0.1 | 97.0 | 2.9 | 89.5 | extremely small particles |
| | 40° C. for 14 days | 0.1 | 95.6 | 4.3 | 82.8 | clear |
| 0.2 mg/ml polysorbate 80 | 0 | 0.2 | 97.4 | 2.4 | 85.3 | clear |
| | freezing-thawing 5 times | 0.1 | 97.1 | 2.8 | 87.5 | extremely small particles |
| | 40° C. for 14 days | 0.2 | 95.3 | 4.5 | 80.9 | clear |
| 0.4 mg/ml polysorbate 80 | 0 | 0.2 | 97.4 | 2.4 | 86.0 | clear |
| | freezing-thawing 5 times | 0.2 | 96.9 | 3.0 | 88.1 | extremely small particles |
| | 40° C. for 14 days | 0.1 | 95.4 | 4.4 | 82.0 | clear |

Example 3

Pharmaceutical formulations comprising IL-15 protein complex 3 at a concentration of 1 mg/mL, 10 mM citric acid-sodium citrate were prepared in buffers (pH 5.5) containing α,α-trehalose dihydrate and sucrose, respectively. Each formulation was filtered and filled into a 2 mL vial at 1 mL/vial, plugged with a stopper, capped and sealed. The samples were subjected to forced degradation testing, such as by placing at 40° C. high temperature and repeated freezing-thawing. The results showed that the stability of IL-15 protein complex 3 in trehalose system is superior to that in sucrose system.

TABLE 3

Results of screening sugars for the stability of IL-15 protein complex 3

| Type and concentration of saccharides | Experimental conditions | SEC (%) polymer | SEC (%) monomer | SEC (%) fragment | Non-reduced CE-SDS(%) | appearance |
|---|---|---|---|---|---|---|
| 6% trehalose | 0 | 0.2 | 97.5 | 2.3 | 87.2 | clear |
|  | freezing-thawing 5 times | 0.2 | 97.0 | 2.8 | 88.9 | extremely fine particles |
|  | 40° C. for 14 days | 0.3 | 95.0 | 4.7 | 82.5 | Filamentous particle |
| 9% trehalose | 0 | 0.1 | 97.6 | 2.3 | 85.3 | clear |
|  | freezing-thawing 5 times | 0.2 | 96.8 | 3.0 | 88.7 | extremely fine particles |
|  | 40° C. for 14 days | 0.1 | 95.3 | 4.6 | 85.6 | Filamentous particle |
| 6% sucrose | 0 | 0.1 | 97.4 | 2.4 | 84.9 | clear |
|  | freezing-thawing 5 times | 0.2 | 96.9 | 2.9 | 87.8 | extremely fine particles |
|  | 40° C. for 14 days | 0.2 | 95.4 | 4.4 | 81.7 | Filamentous particle |
| 9% sucrose | 0 | 0.2 | 97.3 | 2.5 | 86.7 | clear |
|  | freezing-thawing 5 times | 0.2 | 96.8 | 3.0 | 87.5 | extremely fine particles |
|  | 40° C. for 14 days | 0.2 | 94.8 | 5.0 | 79.9 | Filamentous particle |

Note:
In the present disclosure, 6% of trehalose is 60 mg/ml; and 9% is 90 mg/ml.

Example 4: Optimization of the formulation

Figure 2:
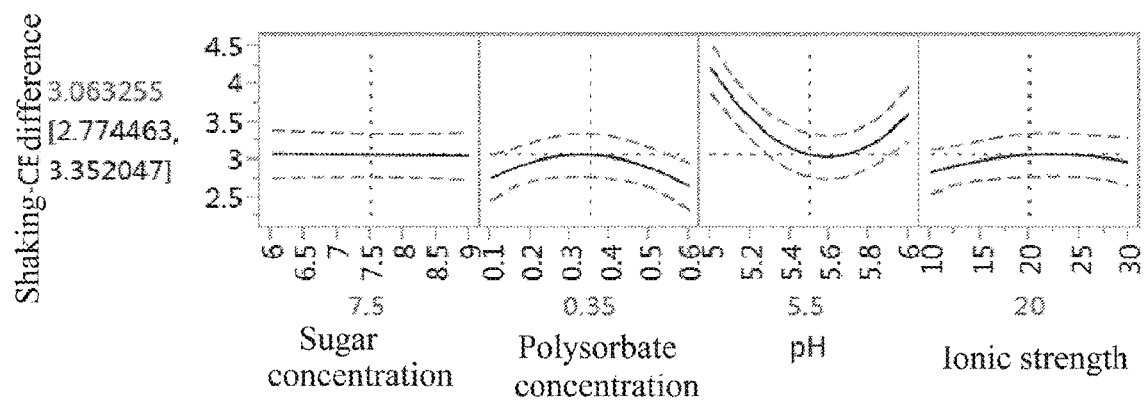
FIG. 2 is a fitting curve chart indicating the difference in purity values after shaking when compared with that at D0, by using non-reducing CE-SDS.
Figure 3:
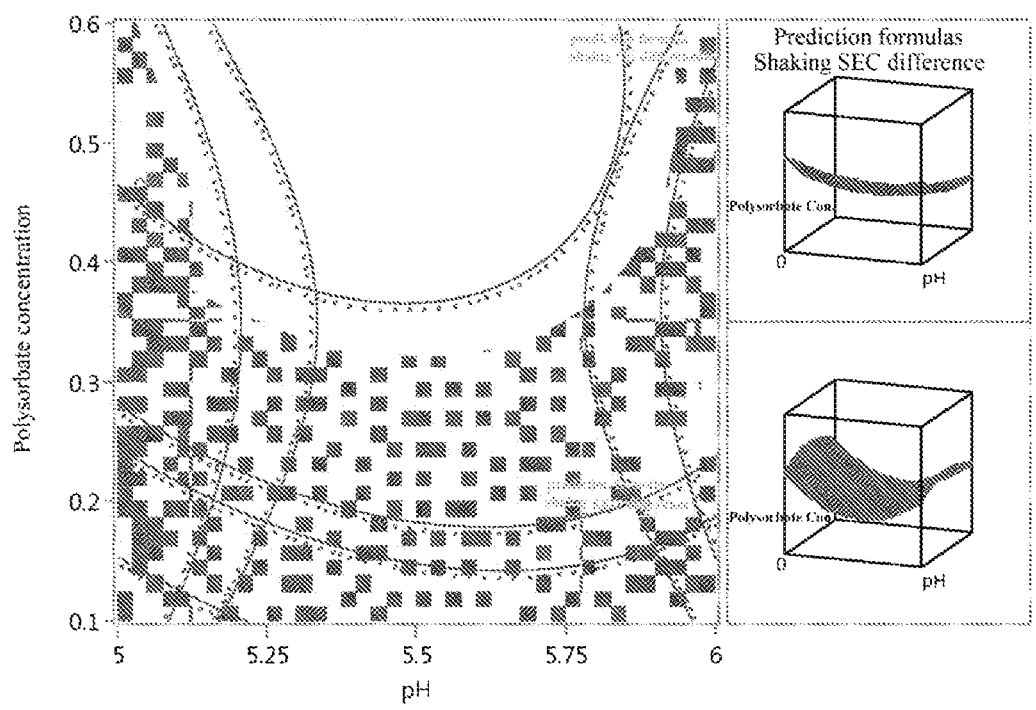
FIG. 3 is a contour map showing the difference in values for SEC and non-reducing CE-SDS after shaking.

In order to further optimize the concentration of trehalose and polysorbate 20, ionic strength and pH, the DOE experiment was designed by using JMP software, and a series of formulations were obtained by using RSM model, wherein the protein concentration was 1 mg/mL. The solution was subjected to forced degradation method, wherein SEC and non-reduced CE-SDS were used as evaluation indexes, and the results were statistically analyzed by least squares test. The DOE parameters were shown in Table 4. The test formulations and results were shown in Tables 5 and 6. Statistical analysis results were shown in FIGS. 1 to 3.

TABLE 4

Factors and levels designed in DOE

| Factor | level | response |
|---|---|---|
| pH | 5.0-6.0 | 40° C. for 20 days, |
| ionic strength | 10-30 mM | freezing-thawing 5 times |
| trehalose | 6-9% | Shaking (300 rpm, 4° C.) |
| polysorbate 20 | 0.1-0.6 mg/ml | SEC, CE-SDS (non-reduced) |

TABLE 5

Formulations of IL-15 Protein Complex 3 designed by DOE

| No. | Buffer | pH | ionic strength(mM) | Concentration of saccharide (%) | Concentration of polysorbate 20 mg/ml |
|---|---|---|---|---|---|
| 01 | citric acid-sodium citrate | 5 | 10 | 9 | 0.6 |
| 02 |  | 5 | 30 | 9 | 0.6 |
| 03 |  | 6 | 20 | 6 | 0.1 |
| 04 |  | 5.5 | 30 | 7.5 | 0.35 |
| 05 |  | 6 | 10 | 6 | 0.6 |

TABLE 5-continued

Formulations of IL-15 Protein Complex 3 designed by DOE

| No. | Buffer | pH | ionic strength(mM) | Concentration of saccharide (%) | Concentration of polysorbate 20 mg/ml |
|---|---|---|---|---|---|
| 06 |  | 5.5 | 20 | 7.5 | 0.35 |
| 07 |  | 5.5 | 20 | 9 | 0.6 |
| 08 |  | 6 | 30 | 9 | 0.1 |
| 09 |  | 5 | 20 | 7.5 | 0.6 |
| 10 |  | 5 | 10 | 6 | 0.35 |
| 11 |  | 5.5 | 30 | 6 | 0.6 |
| 12 |  | 6 | 30 | 7.5 | 0.6 |
| 13 |  | 5 | 20 | 9 | 0.1 |
| 14 |  | 5 | 30 | 6 | 0.1 |
| 15 |  | 5.5 | 10 | 7.5 | 0.1 |
| 16 |  | 6 | 10 | 9 | 0.35 |

Note:
In the present disclosure, 6% of trehalose is 60 mg/ml; and 9% is 90 mg/ml. Other units are converted in a similar way.

TABLE 6

Results of the screened formulations by DOE

| | Purity of SEC monomer (%) | | | | Non-reduced CE-SDS(%) | | | |
|---|---|---|---|---|---|---|---|---|
| No. | 0 | freezing-thawing 5 times | 40° C. for 20 days | shaking for 15 days | 0 | freezing-thawing 5 times | 40° C. for 20 days | shaking for 15 days |
| 01 | 96.0 | 97.0 | 92.1 | 95.8 | 94.1 | 94.9 | 90.3 | 92.1 |
| 02 | 95.9 | 96.9 | 92.5 | 96.3 | 94.7 | 95.6 | 90.8 | 93.4 |
| 03 | 96.1 | 96.6 | 91.3 | 93.6 | 92.0 | 92.9 | 88.4 | 89.8 |
| 04 | 96.1 | 96.9 | 91.9 | 96.2 | 93.6 | 94.2 | 90.5 | 92.3 |
| 05 | 96.0 | 96.8 | 92.0 | 95.9 | 92.8 | 93.9 | 89.4 | 90.1 |
| 06 | 96.4 | 97.0 | 93.8 | 96.3 | 93.3 | 94.5 | 90.3 | 91.6 |
| 07 | 96.1 | 97.2 | 92.1 | 96.0 | 93.6 | 94.7 | 91.0 | 92.0 |
| 08 | 95.8 | 96.5 | 92.7 | 95.9 | 91.8 | 93.2 | 89.0 | 90.6 |
| 09 | 96.3 | 96.6 | 93.0 | 96.7 | 94.7 | 94.9 | 90.9 | 93.8 |
| 10 | 96.4 | 96.9 | 91.6 | 95.9 | 94.1 | 94.5 | 90.6 | 91.8 |
| 11 | 96.0 | 96.7 | 93.6 | 96.2 | 93.9 | 94.8 | 91.3 | 93.1 |
| 12 | 96.4 | 96.6 | 92.9 | 95.6 | 93.0 | 93.9 | 90.0 | 91.4 |
| 13 | 96.1 | 96.5 | 92.9 | 94.4 | 94.2 | 94.1 | 89.9 | 92.4 |
| 14 | 96.0 | 96.7 | 92.7 | 93.4 | 94.5 | 94.8 | 90.7 | 93.2 |
| 15 | 95.6 | 96.5 | 94.1 | 94.0 | 93.3 | 93.7 | 90.8 | 90.7 |
| 16 | 95.9 | 96.8 | 91.0 | 95.4 | 92.4 | 93.3 | 89.2 | 89.6 |

Data obtained from forced degradation were fitted and the results were as follows:

The difference in values of SEC monomer purity between D0 and D15 (after shaking) were fitted (the difference value is considered as 0, when it is negative), $R^2>0.99$, $P<0.05$, the model was valid. The results were shown in FIG. 1.

By using non-reduced CE-SDS, the difference in values of purity between D0 and D15 (after shaking) were fitted, $R^2>0.98$, $P<0.05$, and the model was valid. The results were shown in FIG. 2.

For other data, fitting was invalid.

In order to ensure good compactibility and suitable osmolality of the lyophilized formulation, the concentration of the trehalose was set to 7.5±0.5% (75±5 mg/ml). It was found that the 10±2 mM ionic strength had sufficient buffering capacity.

The concentration of trehalose was set to 7.5% (75 mg/ml), the ionic strength was set to 10 mM, the pH was plotted on the abscissa, the concentration of polysorbate was plotted on the ordinate, and a contour map was plotted to show the difference in values of SEC after shaking and non-reduced CE-SDS. The results were shown in FIG. 3. Based on the results shown in the figure in combination with the isoelectric point of the protein complex, it can be seen that a preferred pH range for the formulation is from pH5.15 to pH5.25, and the concentration of polysorbate is 0.4-0.6 mg/ml.

Example 5

IL-15 Protein Complex 3 was formulated at 1.0 mg/mL in 10 mM citric acid-sodium citrate (pH 5.2), 75 mg/mL α,α-trehalose dihydrate, 0.5 mg/mL polysorbate 20, pH 5.2. The protein was filled into a 2 mL vial at 1.1 mL/vial, lyophilized at primary drying temperature of −25° C., −20° C. and −15° C., respectively, and sealed with a lyophilized rubber stopper for testing. The results showed that appearance of all reconstituted solutions at various temperature met the requirements, and the appearance of the formulation lyophilized at −25° C. was better, and the powder cake was full without collapse.

TABLE 7

Steps for lyophilization of the formulation

| Parameters for lyophilization process | Temperature (° C.) | vacuum degree (mBar) |
|---|---|---|
| pre-freezing | 5 | N/A |
| | −45 | N/A |
| primary drying | −25 | 0.08 |
| secondary drying | 25 | 0.01 |

Example 6

IL-15 Protein Complex 3 was formulated at 1.0 mg/mL in 10 mM citric acid-sodium citrate (pH 5.2), 75 mg/mL α,α-trehalose dihydrate, 0.5 mg/mL polysorbate 20, pH 5.2. The formulations were filled in glass vials, liquid storage bags and 316L stainless steel tanks, respectively, and placed at 2-8° C. and 25° C., respectively for 24 hours. Analysis of appearance, pH, protein content and purity indicated that IL-15 protein complex 3 was stable within 24 hours. The formulation was compatible with glass vials, stainless steel tanks and liquid storage bags.

TABLE 8

Stability of IL-15 protein complex 3 in various contacting materials

| Temperature | Grouping | Time (h) | Appearance | pH | Content (mg/ml) | Purity of SEC monomer (%) | Non-reduced CE-SDS (%) |
|---|---|---|---|---|---|---|---|
| 2-8° C. | glass | 0 | clear | 5.28 | 1.043 | 99.83 | 96.4 |
| | | 8 | clear | 5.27 | 1.031 | 99.84 | 96.2 |
| | | 24 | clear | 5.28 | 1.030 | 99.82 | 96.0 |
| | liquid storage bags | 8 | clear | 5.27 | 1.049 | 99.80 | 96.6 |
| | | 24 | clear | 5.27 | 1.027 | 99.82 | 96.1 |
| | stainless steel | 8 | clear | 5.27 | 1.046 | 99.82 | 96.6 |
| | | 24 | clear | 5.27 | 1.056 | 99.90 | 95.3 |

TABLE 8-continued

Stability of IL-15 protein complex 3 in various contacting materials

| Temperature | Grouping | Time (h) | Appearance | pH | Content (mg/ml) | Purity of SEC monomer (%) | Non-reduced CE-SDS (%) |
|---|---|---|---|---|---|---|---|
| 25° C. | glass | 8 | clear | 5.28 | 1.032 | 99.83 | 96.9 |
| | | 24 | clear | 5.28 | 1.026 | 99.79 | 95.3 |
| | liquid storage bags | 8 | clear | 5.28 | 1.029 | 99.84 | 97.0 |
| | | 24 | clear | 5.25 | 1.034 | 99.78 | 96.6 |
| | stainless steel | 8 | clear | 5.29 | 1.032 | 99.76 | 96.0 |
| | | 24 | clear | 5.27 | 1.057 | 99.88 | 95.0 |

Example 7

Other alternative pharmaceutical compositions (formulations) or reconstituted solutions Stable pharmaceutical formulations further provided comprise:

(1) 5 mg/ml IL-15 protein complex 3, 75 mg/ml trehalose, 0.5 mg/ml polysorbate 20, and 10 mM citric acid-sodium citrate buffer, with final pH of 5.2;

(2) 10 mg/ml IL-15 protein complex 3, 75 mg/ml trehalose, 0.5 mg/ml polysorbate 20, and 10 mM citric acid-sodium citrate buffer, with final pH of 5.2;

(3) 10 mg/ml IL-15 protein complex 3, 75 mg/ml sucrose, 0.5 mg/ml polysorbate 20, and 10 mM citric acid-sodium citrate buffer, with final pH of 5.25;

(4) 0.9 mg/ml IL-15 protein complex 3, 60 mg/ml trehalose, 0.1 mg/ml polysorbate 20, and 20 mM citric acid-sodium citrate buffer (pH 5.0);

(5) 1 mg/ml IL-15 protein complex 3, 75 mg/ml trehalose, 0.5 mg/ml polysorbate 20, and 10 mM citric acid-sodium citrate buffer (pH 5.2);

(6) 1.1 mg/ml IL-15 protein complex 3, 90 mg/ml trehalose, 0.6 mg/ml polysorbate 20, and 30 mM citric acid-sodium citrate buffer (pH 5.5);

(7) 0.9 mg/ml IL-15 protein complex 3, 60 mg/ml trehalose, 0.1 mg/ml polysorbate 20, and 20 mM citric acid-sodium citrate buffer, with final pH of 5.0;

(8) 1.1 mg/ml IL-15 protein complex 3, 90 mg/ml trehalose, 0.6 mg/ml polysorbate 20, and 30 mM citric acid-sodium citrate buffer, with final pH of 5.5;

(9) 0.5 mg/ml IL-15 protein complex 3, 65 mg/ml trehalose, 0.3 mg/ml polysorbate 20 (pH 5.3), and 15 mM citric acid-sodium citrate buffer.

The invention claimed is:

1. A pharmaceutical composition comprising:
   (a) 0.9 mg/ml to 1.1 mg/ml IL-15 protein complex,
   (b) 10 mM±2 mM citrate buffer,
   (c) 75 mg/ml±5 mg/ml α,α trehalose dihydrate, and
   (d) 0.5 mg/ml polysorbate 20, the pH of the pharmaceutical composition is 5.15 to 5.25:
   wherein the IL-15 protein complex consists of IL-15 shown as SEQ ID NO: 1 and a fusion protein of IL-15 receptor shown as SEQ ID NO: 2.

2. A lyophilized formulation, wherein the lyophilized formulation can be reconstituted to form the pharmaceutical composition according to claim 1.

3. A lyophilized formulation comprising an IL-15 protein complex prepared by lyophilizing the pharmaceutical composition according to claim 1.

4. A reconstituted solution comprising an IL-15 protein complex prepared by reconstituting the lyophilized formulation of claim 3.

5. The reconstituted solution according to claim 4, wherein the concentration of the IL-15 protein complex is from 1 mg/ml to 1.1 mg/ml.

6. A reconstituted solution according to claim 4, wherein the pH of the reconstituted solution is from 5.15 to 5.25.

7. The reconstituted solution according to claim 4, wherein the concentration of the buffer is 10 mM±2 mM.

8. The reconstituted solution according to claim 4, wherein the α, α trehalose dihydrate is present at a concentration of 75 mg/ml±5 mg/ml.

9. The reconstituted solution according to claim 4, wherein the polysorbate 20 is present at a concentration 0.5 mg/ml.

10. A product, comprising a container containing the pharmaceutical composition of claim 1.

11. A pharmaceutical composition comprising:
(a) 1 mg/ml IL-15 protein complex,
(b) 10 mM citrate buffer,
(c) 75 mg/ml α, α trehalose dihydrate, and
(d) 0.5 mg/ml polysorbate 20, the pH of the pharmaceutical composition is 5.2,
wherein the IL-15 protein complex consists of IL-15 shown as SEQ ID NO: 1 and a fusion protein of IL-15 receptor shown as SEQ ID NO: 2.

12. A lyophilized formulation, wherein the lyophilized formulation can be reconstituted to form the pharmaceutical composition according to claim 11.

13. The pharmaceutical composition according to claim 1, wherein the pharmaceutical composition is stable for at least 14 days at 40° C., and wherein no more than about 10% of monomers in the protein complex are degraded, as measured by SEC.

14. The pharmaceutical composition according to claim 11, wherein the pharmaceutical composition is stable for at least 14 days at 40° C., and wherein no more than about 10% of monomers in the protein complex are degraded, as measured by SEC.

\* \* \* \* \*